(12) United States Patent
Beller et al.

(10) Patent No.: US 9,622,808 B2
(45) Date of Patent: Apr. 18, 2017

(54) DEVICE FOR CONTACTLESS COMMUNICATION AND USE OF A MEMORY DEVICE

(75) Inventors: Juergen Beller, Gomaringen (DE); Uwe Schnitzler, Tuebingen (DE); Peter Selig, Hechingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 950 days.

(21) Appl. No.: 12/747,586

(22) PCT Filed: Dec. 11, 2008

(86) PCT No.: PCT/EP2008/010550
§ 371 (c)(1),
(2), (4) Date: Jun. 11, 2010

(87) PCT Pub. No.: WO2009/074329
PCT Pub. Date: Jun. 18, 2009

(65) Prior Publication Data
US 2010/0262139 A1 Oct. 14, 2010

(30) Foreign Application Priority Data

Dec. 12, 2007 (DE) .......... 10 2007 059 619
Dec. 10, 2008 (DE) .......... 10 2008 061 418

(51) Int. Cl.
*A61B 18/14* (2006.01)
*A61B 18/12* (2006.01)
(Continued)

(52) U.S. Cl.
CPC .......... *A61B 18/1206* (2013.01); *A61B 90/98* (2016.02); *A61B 17/3203* (2013.01);
(Continued)

(58) Field of Classification Search
CPC ...... A61B 2018/00636; A61B 2562/08; A61B 2562/226; A61B 2562/227; A61B 2019/448
(Continued)

(56) References Cited

U.S. PATENT DOCUMENTS 5,383,460 A    1/1995  Jang et al.
5,400,267 A *  3/1995  Denen et al. .................. 702/59
(Continued)

FOREIGN PATENT DOCUMENTS

DE          92 00 452 U1    6/1992
DE   10 2005 011 385 A1   12/2005
(Continued)

*Primary Examiner* — Jocelyn D Ram
(74) *Attorney, Agent, or Firm* — Blank Rome LLP

(57) ABSTRACT

The invention relates to a device for contactless communication between a surgical apparatus and at least one surgical instrument. The surgical apparatus comprises a control and evaluation device to which is assigned a writing or reading device which is connected to an antenna for the apparatus. The instrument is assigned at least one writable and readable memory device, embodied as an RFID transponder, which is connected to an antenna for the instrument, so that data can be exchanged between the writing or reading device of the surgical apparatus and the memory device of the instrument by means of wireless communication.

16 Claims, 4 Drawing Sheets

(51) Int. Cl.
*A61B 90/98* (2016.01)
*A61B 17/3203* (2006.01)
*A61B 17/00* (2006.01)
*A61B 18/00* (2006.01)
*A61B 90/40* (2016.01)
*A61B 90/00* (2016.01)

(52) U.S. Cl.
CPC ..... *A61B 90/40* (2016.02); *A61B 2017/00084* (2013.01); *A61B 2018/00916* (2013.01); *A61B 2018/00988* (2013.01); *A61B 2090/0813* (2016.02)

(58) Field of Classification Search
USPC .................................................. 606/32–52
See application file for complete search history.

(56) References Cited

U.S. PATENT DOCUMENTS

| | | | |
|---|---|---|---|
| 5,505,729 A | 4/1996 | Rau | |
| 7,128,741 B1* | 10/2006 | Isaacson et al. | 606/41 |
| 7,691,097 B2* | 4/2010 | Miyazawa | 606/1 |
| 7,796,040 B2* | 9/2010 | Mezhinsky et al. | 340/572.1 |
| 2001/0051766 A1 | 12/2001 | Gazdzinski | |
| 2002/0128646 A1* | 9/2002 | Zhang et al. | 606/41 |
| 2002/0165541 A1* | 11/2002 | Whitman | 606/48 |
| 2002/0183686 A1* | 12/2002 | Darvish et al. | 604/21 |
| 2003/0093103 A1* | 5/2003 | Malackowski et al. | 606/170 |
| 2004/0122419 A1* | 6/2004 | Neuberger | 606/10 |
| 2006/0129140 A1* | 6/2006 | Todd et al. | 606/1 |
| 2006/0145871 A1* | 7/2006 | Donati et al. | 340/572.8 |
| 2007/0066978 A1 | 3/2007 | Schafer et al. | |
| 2007/0167941 A1 | 7/2007 | Hamel et al. | |
| 2008/0154251 A1* | 6/2008 | Stuart et al. | 606/13 |
| 2008/0167522 A1* | 7/2008 | Giordano et al. | 600/104 |
| 2008/0167672 A1* | 7/2008 | Giordano et al. | 606/167 |
| 2008/0200844 A1* | 8/2008 | Millahn et al. | 600/595 |
| 2008/0243157 A1* | 10/2008 | Klein et al. | 606/167 |
| 2008/0262476 A1* | 10/2008 | Krause et al. | 604/540 |
| 2008/0281322 A1* | 11/2008 | Sherman et al. | 606/42 |
| 2009/0275940 A1* | 11/2009 | Malackowski et al. | 606/42 |
| 2011/0208206 A1* | 8/2011 | Diamant et al. | 606/128 |
| 2014/0236138 A1* | 8/2014 | Tran et al. | 606/33 |
| 2014/0276603 A1* | 9/2014 | Magee et al. | 604/508 |

FOREIGN PATENT DOCUMENTS

| | | |
|---|---|---|
| DE | 10 2005 003 171 A1 | 8/2006 |
| DE | 10 2005 044 918 A1 | 2/2007 |
| DE | 10 2006 002 418 A1 | 7/2007 |
| EP | 1 410 766 A1 | 4/2004 |
| EP | 1 943 957 A2 | 7/2008 |
| EP | 1 958 586 A1 | 8/2008 |
| JP | 2004-65674 A | 3/2004 |
| JP | 2004-290462 A | 10/2004 |
| JP | 2005-144169 A | 6/2005 |
| WO | WO 00/24318 A1 | 5/2000 |
| WO | WO 2006/031632 A2 | 3/2006 |
| WO | WO 2006/060781 A1 | 6/2006 |

* cited by examiner

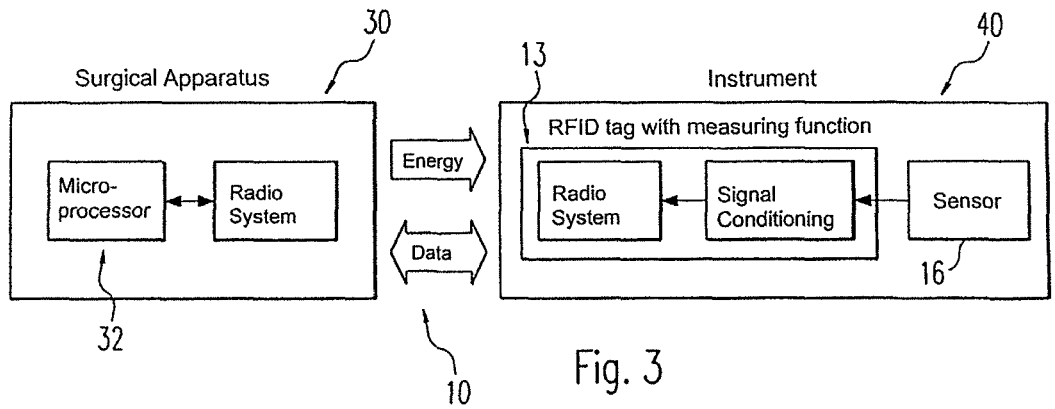
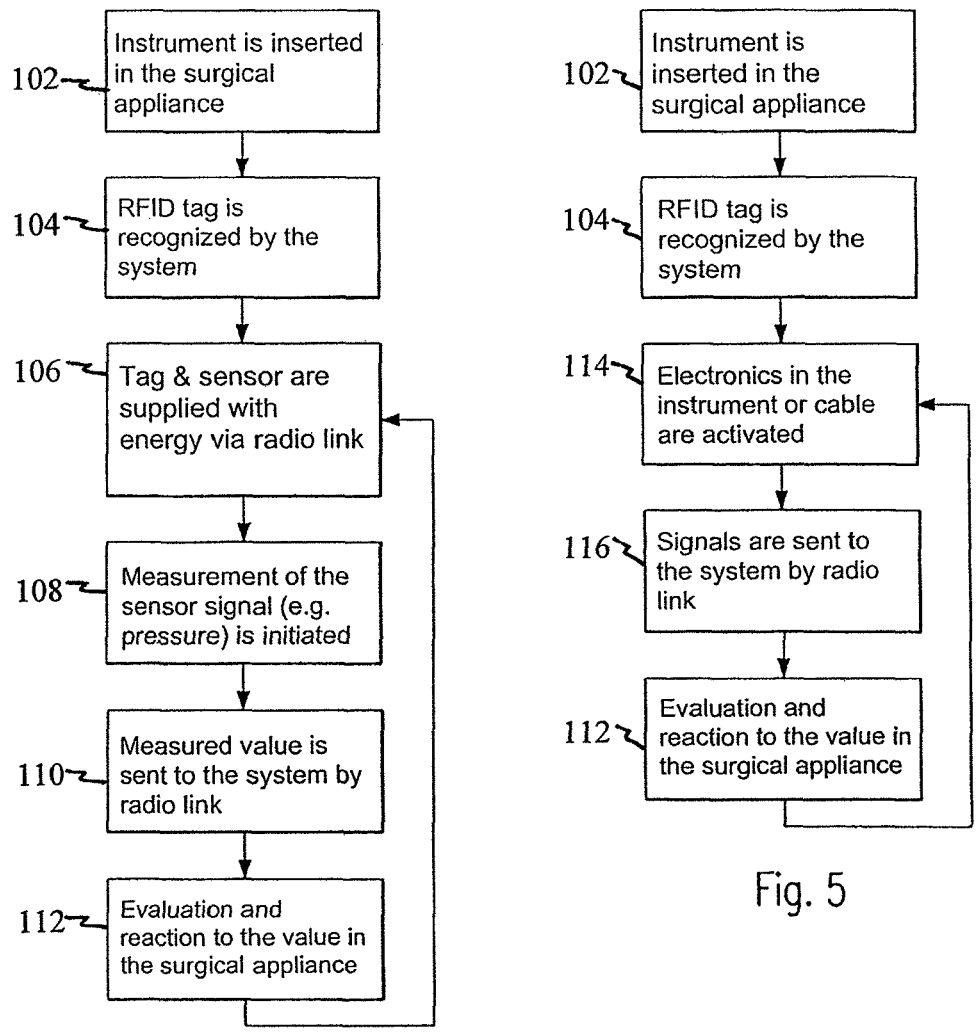
Fig. 4
Fig. 5

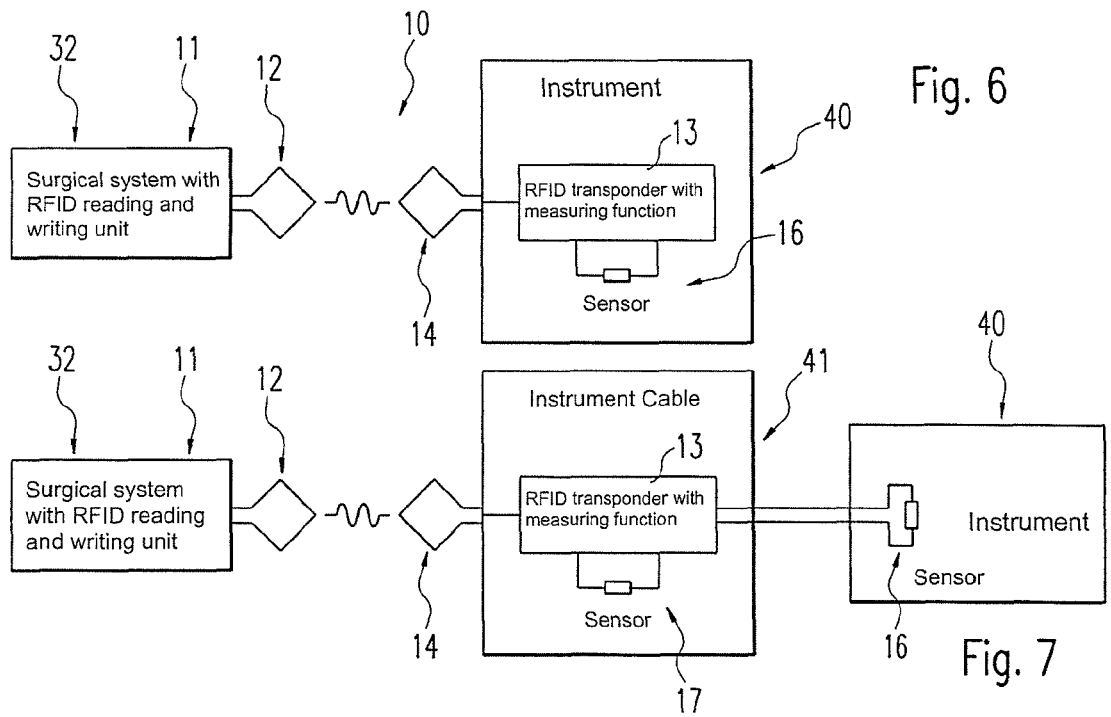
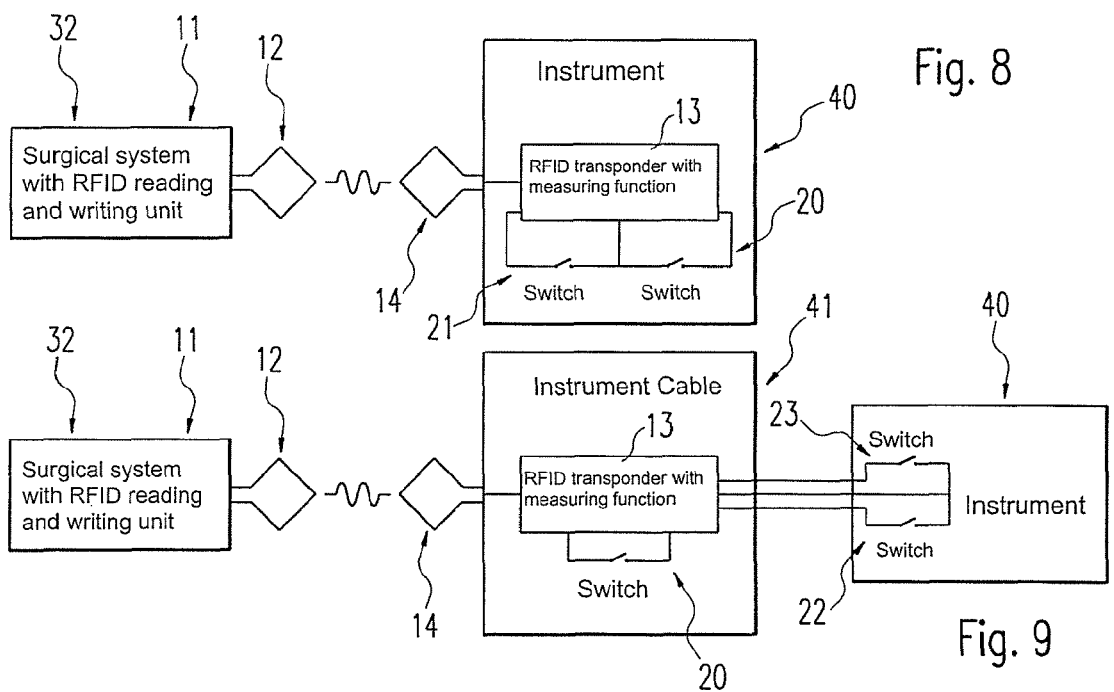

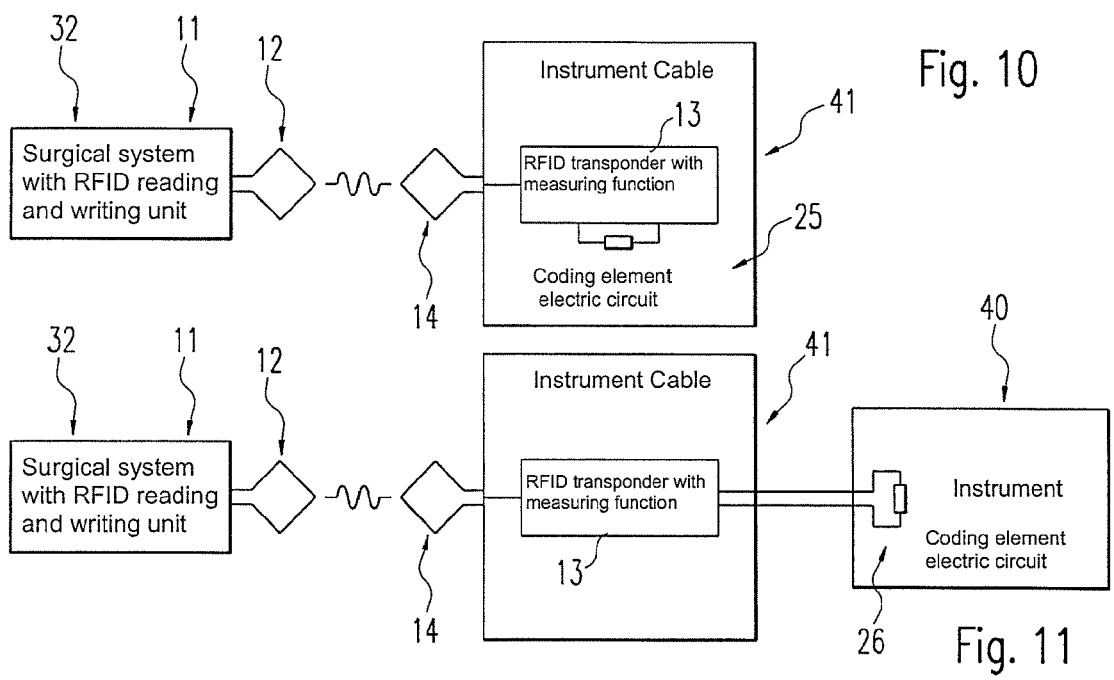

DEVICE FOR CONTACTLESS COMMUNICATION AND USE OF A MEMORY DEVICE

BACKGROUND OF THE INVENTION

The invention relates to a device for contactless communication between a surgical apparatus and at least one surgical instrument or similar accessory that can be used with said surgical apparatus and the use of a writable and readable memory device that is connected to an antenna for the instrument.

In the fields of high-frequency surgery ("HF surgery"), cryosurgery or even water jet surgery, a plurality of instruments are used which may be operated within a surgical system with a surgical apparatus. Instruments of this kind are, for example, instruments comprising electrodes for HF surgery or applicators for supplying water to the area on which the operation is performed. Probes are used in the field of endoscopy.

Due to the plurality of extremely different instruments or accessories in a surgical system, it is necessary to provide an automatic recognition of the instruments so that the corresponding surgical apparatus can supply the parameters required for the operation of the respective instrument, such as the suitable voltage or water pressure. Otherwise, users would have to enter or set all parameters themselves by hand, i.e., before the actual use, a time-consuming configuration phase would be necessary. In addition, manual input can represent an error source which is dangerous for the patient, in particular because the user will not have all parameter values at hand.

Various solutions for automatic instrument recognition are known from the prior art. For example, electronic memories, such as an electrically erasable programmable read-only memory ("EEPROM"), are provided on the instrument in order to be able to transmit data via the instrument to the surgical apparatus. Instrument recognition is effected by cable connection or also by wireless means.

The EEPROM requires at least one additional plug-in contact in order to be able to establish the electric connection between the apparatus and the memory chip in the instrument or in the accessory. This means that use in a standard plug-in connector, such as a neutral-electrode connector or 3-pin connector known from HF surgery, is not possible.

Known from DE 10 2005 044 918 A1, is a device for contactless identification and communication between a HF generator and an instrument connected thereto. It is now possible to exchange information by radio contact between the instrument and HF generator via a transponder device (with an antenna for the instrument), arranged in an instrument connector, and a writing and reading unit (with an antenna for the generator), again arranged on the generator. However, in DE 10 2005 044 918 A1, the writable and readable data memory in the transponder device is only suitable for a restricted exchange of information.

BRIEF SUMMARY OF THE INVENTION

The invention is based on the object of disclosing a device as described above but where data exchange is improved, in particular expanded, and hence the patients' safety is improved.

This object is achieved by a device for contactless communication between a surgical apparatus and at least one surgical instrument or similar accessory that can be used with said surgical apparatus and by the use of a writable and readable memory device connected to an antenna for the instrument. With respect to the device, the object is a device for contactless communication between a surgical apparatus and at least one surgical instrument or similar accessory that may be used with said apparatus, wherein the surgical apparatus comprises a control and evaluation device to which is assigned at least one writing and/or reading device connected to an antenna for the apparatus, wherein the instrument is assigned at least one writable and readable memory device. The at least one writable and readable memory device is embodied as a radio frequency identification ("RFID") transponder (or the transponder encompasses the memory device) connected to an antenna for the instrument, so that data may be exchanged between the writing and/or reading device of the surgical apparatus and the memory device of the instrument by means of wireless communication. The instrument comprises a measuring and/or actuating device which is assigned to the memory device and is embodied to influence the memory device in such a way that at least one parameter may be acquired on and/or in the instrument and/or on tissue to be treated for transmission to the surgical apparatus. At least one signal or data for influencing the function of the instrument can also be transmitted from the surgical apparatus to the instrument via the RFID system.

An essential point of the invention is the fact that, due to the interaction of the transponder (also called a "tag") and the measuring and/or actuating device, it is now possible not only to transmit electronically stored information between the instrument and surgical apparatus or between the writing and/or reading device and the writable and readable memory device, but also to evaluate and transmit measured data and digital signals. This is possible insofar that, apart from a writable and readable memory area, the transponder component also comprises digital and analog interfaces, with which sensors, actuators and general electronic components can be operated and evaluated on the instrument or in the instrument cable (for example, a tag with integrated measuring technology). To this end, the tags comprise interfaces via which the measured data can be acquired. This means that further essential information can be transmitted in an extremely simple way to the surgical apparatus without additional lines having to be provided for this purpose. Obviously, data are also transmitted in the reverse direction, that is from the surgical apparatus to the instrument. The measuring device enables the acquisition of a comprehensive data spectrum and therefore also enables comprehensive patient care. In addition, the use of RFID technology data transmission can also take place with surgical systems, which do not work with a high-frequency current even if no electric contacts are provided for the instruments or the accessories. For example, instruments or accessories for cryosurgery or water jet surgery only have a pneumatic or liquid connection. Despite this, data transfer is possible with the device according to the invention.

Specifically, this now means that the measuring and/or actuating device is assigned to the memory device in such a way that the data it acquires (for example, measured values or even detected actions) can be transmitted to the surgical apparatus or the writing and/or reading device so that subsequently—if necessary—it is possible to make settings on the surgical apparatus or on the generator (automatically or optionally, even manually) and the instrument is subsequently supplied via the instrument cable for example, with another suitable voltage or another current. In addition, (with the transmission of corresponding parameters via the instrument cable or even without such a transmission) data can be transmitted via the RFID system from the surgical apparatus or from the writing and/or reading device to the instrument, so that, for example, the actuating device can be or is actuated via the tag. However, the data transmitted from the writing and/or reading device can also effect reactions on the instrument without the measuring and/or actuating device being active. In each case, data transfer can take place in both directions, wherein corresponding parameters can be provided on the instrument via the instrument cable simultaneously with the data transfer or exclusively (i.e., without data transfer from the writing and/or reading device to the memory device).

The RFID technology with the combined measuring and/or actuating device is in particular also suitable for instruments which may be connected to the surgical apparatus by means of a standard plug-in connector. These plug-in connectors do not have sufficient contacts for the transmission of additional data. The additional data (for example, from the measuring device) can now be transmitted via the RFID system's wireless connection. Within a certain framework, the power supply for the electronics for the instrument can also be provided by this means. The RFID technology offers the opportunity of writing and reading a non-volatile electronic memory (EEPROM) wirelessly via a radio link. Here, the advantage is that the memory does not necessarily require a voltage supply in the form of a battery, since it can draw the necessary electric energy from the radio link's carrier signal.

Reference is made to the fact that the data exchange between the writing and/or reading device and the memory device takes place via the respective antennas, even if this involves a data exchange between the surgical apparatus and the instrument.

In a first embodiment, the writable and readable memory device with the antenna for the instrument is embodied as a transponder IC with a freely programmable microprocessor. This means that with this type of transponder it is possible at any time to enter new data to overwrite or supplement the existing data. For example, this includes operational data, to facilitate the further use of the instrument or the accessory.

A fixed-programmed transponder memory would also be conceivable. This can be advantageous if it is desired to prevent the data in the memory from being changed by the user, for example.

Preferably, the writable and readable memory device with the antenna for the instrument is embodied in a connector device or in a connecting cable in order to connect the instrument to the surgical apparatus. As soon as the instrument is connected to the surgical apparatus, the antenna for the apparatus and the antenna for the instrument are arranged at a suitable distance and in a suitable alignment to each other so that optimum communication is provided between the writing and/or reading device and memory device.

Alternatively, it would obviously also be possible to arrange the transponder with the antenna for the instrument in the instrument. Here, however, the communication could be complicated by different positions of the instrument, for example, during a surgical intervention.

During the process of the production of the connector, the tag can be simply cast in the connector which is produced by injection molding, i.e., the complicated assembly and contacting process required for an EEPROM is dispensed with, thus reducing the costs of manufacturing the instrument.

Preferably, the measuring and/or actuating device is assigned at least one sensor arranged on the instrument and the measuring and/or actuating device is embodied in such a way that it acquires a sensor signal from at least one sensor as the parameter. In this way, it is possible to acquire and evaluate data in a simple way, namely via a suitably positioned sensor.

In addition, the measuring and/or actuating device can be assigned at least one actuator arranged on the instrument for influencing the instrument function. An actuator of this kind is, for example, a switch or a spool in a valve in order in this way to regulate or control the operation of the instrument. Preferably, the instrument's memory device will receive the command from the surgical apparatus and forward it via a corresponding interface to the actuator. In this way, therefore, the actuator will be actuated via the transponder.

As soon as, as part of its measuring function, the measuring and/or actuating device has acquired a sensor signal, this signal can be stored in the tag and transmitted to the writing and/or reading device by means of wireless communication. The control and evaluation device in the surgical apparatus evaluates the received signal and can subsequently make a corresponding setting (where necessary) on the surgical apparatus. It is possible, for example, for a radio signal to actuate the actuator via the RFID system in order to in this way operate the instrument by means of radio control, as already explained above.

Preferably, the measuring and/or actuating device or the device for contactless communication is embodied in such a way that the acquisition of the parameter and the influencing of the function of the instrument can be performed independently of each other. This means that both the measuring device and the actuating device can be operated independently of each other. The possible acquisition of a sensor signal can also effect settings on the surgical apparatus without at least one actuator being actuated (it is possible, for example, for a parameter to be acquired by the measuring device and transmitted to the surgical apparatus without an actuator being or becoming active).

Obviously, it is also possible for the measuring and/or actuating device or the device for contactless communication to be embodied in such a way that the influencing of the function of the instrument takes place on the basis of an acquired parameter. Therefore, this can mean, for example, that the measuring device of the measuring and/or actuating device acquires a signal via a sensor. The signal is then transmitted to the writing and/or reading device so that, on the basis of this acquired signal, this is able to control the actuator via the RFID system. The actuator can also be controlled "by wire" via a signal line. The actuation of the measuring device on the basis of an action of the actuator is also possible, i.e., an extremely wide variety of variants can be provided here.

In a further embodiment, the measuring and/or actuating device is embodied in the instrument or in the connecting cable in order to connect the instrument to the surgical apparatus. This facilitates, inter alia, the assignment of the sensors and/or actuators on the instrument.

The measuring and/or actuating device can also be embodied in such a way that it acquires the actuation of a switch (for example, by the surgeon) on the instrument as the parameter. For example, it is therefore possible that, on the actuation of the switch, the surgeon wishes to initiate a process (for example, a change from a coagulation process to a cutting process) and this information can now be transmitted to the surgical apparatus by means of wireless communication. These new settings (for example, an increase in the voltage) will then be made on the surgical apparatus automatically and made available via the electric connection on the instrument, for example.

One embodiment envisages, for example, that the surgical apparatus and the instrument are embodied for water jet surgery and the measuring and/or actuating device is embodied and arranged in such a way that the pressure in a feed line for water onto the tissue to be treated in a water-jet applicator is acquired as a parameter, preferably via the sensor. A sensor on the instrument could also supply information on the prevailing pressure, which is, for example, measured continuously and forward this information to the surgical apparatus or its writing and/or reading device by means of wireless communication. Subsequently, the pressure can be regulated automatically or, optionally, manually (for example, by means of a display on the surgical apparatus).

The control and evaluation device, which is assigned to the surgical apparatus, can evaluate the data acquired from the writing and/or reading device and control the surgical apparatus accordingly in order to initiate the necessary control processes. This ensures, for example, that the correct water pressure is always applied to the area on which the operation is performed.

Preferably, the surgical apparatus and the instrument can be embodied for HF surgery, wherein the measuring and/or actuating device is then embodied and arranged in such a way that the temperature of an electrode in an HF surgical instrument is acquired as a parameter (or even the temperature of the treated tissue) during usage, preferably via the sensor. In this way, the temperature acquisition enables the provision of a suitable voltage for any cutting or coagulation processes.

A further embodiment envisages that the writable and readable memory device is embodied in such a way that data from the instrument relating to sterilisation cycles, use-by dates, instrument recognition or similar data can be read-in and read-out. These data can, for example, be input directly via the writing and/or reading device or the measuring device can acquire the data and store it in the writable and readable memory device of the instrument. In each case, when required, the data can then be made available via the writing and/or reading device.

The measuring device can, for example, be embodied in such a way that it acquires measured values for example, relating to a sterilisation cycle (optionally from an autoclave which also comprises a writing and/or reading device), so that these data may be read out at any time, for example, via the surgical apparatus.

Preferably, the instrument encompasses at least one coding element, which is assigned to the writable and readable memory device and which is embodied in such a way that coding, preferably for the identification of the instrument, can be acquired by the writing and/or reading device on the surgical apparatus. Once again, it is also possible with this embodiment for the corresponding data to be read out directly or for the measuring device to acquire the corresponding coding.

Preferably, the writing and/or reading device with the antenna for the apparatus is embodied in such a way that the data from the instrument and/or the coding may be acquired through a packaging of the instrument, in particular through a sterile packaging. This means the instruments can be checked through the packaging. For example, it is possible to check the type of instrument (instrument recognition), the sterility status, the number of sterilisation cycles or similar parameters. Therefore, a suitable transmission power should be ensured here to enable the data to be acquired.

The use of a writable and readable memory device connected to an antenna for the instrument, in particular an RFID transponder, in a surgical instrument in packaged condition, for the acquisition or reading-in and reading-out of instrument data and their transmission to a receiver is also considered to be inventive.

If the receiver is embodied as a writing and/or reading device of a surgical apparatus connected to an antenna for the apparatus, the data can be transmitted directly from the instrument to the surgical apparatus or to the writing and/or reading device or can be requested by said apparatus, even if the instrument is not yet connected for use with the surgical apparatus. The writing and/or reading device is, for example, assigned to the control and evaluation device of the surgical apparatus, which evaluates the data from the instrument accordingly and optionally initiates further processes on the basis of the received data (even if this is only to show information on a display). It is in particular advantageous for data on the sterility, status of the instrument to be determined so that the user recognises whether the instrument has been sterilised correctly or not.

With respect to the device, the object is also achieved in that a device for contactless communication between a receiver, in particular a surgical apparatus, and at least one surgical instrument or similar accessory that can be used with said surgical apparatus is provided, wherein the receiver comprises a control and evaluation device, which is assigned at least one writing and/or reading device, which is connected to an antenna for the apparatus. The instrument is assigned at least one writable and readable memory device, in particular embodied as an RFID transponder (or the transponder encompasses the memory device), which is connected to an antenna for the instrument so that data may be exchanged between the receiver and the memory device of the instrument by means of wireless communication. The writing and/or reading device with the antenna for the apparatus is embodied in such a way that the communication can take place between the receiver and a packaged instrument, in particular a sterile-packaged instrument.

Here 'receiver' does not solely mean the writing and/or reading device with the antenna, but, more comprehensively, the device comprising the writing and/or reading device with the antenna.

This device may be use to check packaged instruments, in particular with respect to their sterility status. This means that sterile products with a limited "use-by date" can be checked electronically to see if they are suitable to use without damaging the sterile packaging or rejected by the device if they are used following the expiry deadline. Even in the case of a plurality of accessories in one packaging unit, it will be possible to recognise and distinguish them. It is hence possible to check a packaging with sterilised instruments to ensure it is complete without having to open the sterile packaging. This is a significant advantage particularly during handling in the hospital and also throughout the entire logistics cycle. No further electric connection of the instrument to the surgical apparatus is required for this. Instead, information on the instrument can be read out via the writing and/or reading device with the antenna for the apparatus in order, for example, to check whether the instrument is suitable for the desired use. For example, as described above, in addition to instrument recognition it is also possible to receive data on the sterility status without having to remove the instrument from the packaging.

The wireless memory technology makes it possible to precisely monitor the number of completed sterilisation cycles independently of the place of installation of the RFID system in the instrument or in the accessory. To this end, it is only necessary to provide a corresponding writing and/or reading device on the autoclave, which reads the dates in the tag on sterilisation, amends a stored sterilisation counter and rewrites the values. Therefore, the instruments can be recognised in a contactless manner on sterilisation and reprogrammed. This enables the implementation of a "genuine" sterilisation cycle counter with which an RFID terminal is integrated in the RFID system and accesses a counting function in the tag.

In one embodiment, the tags can inter alia be provided in film form or as a very economical, printable polymer circuit on, for example, a neutral electrode. Polymer circuits are so inexpensive that implementation on electrodes for single use is conceivable. With this arrangement, the reading unit is preferably located in the clamping device of the neutral electrode cable, so that the electrode can be directly recognised. This makes it possible to determine the precise type of neutral electrode.

BRIEF DESCRIPTION OF DRAWINGS

The following describes the invention with reference to exemplary embodiments which are explained in more detail with reference to the drawings.

FIG. 3 is a simplified representation of the device according to embodiments of the invention with a surgical apparatus and instrument to explain the measuring function according to FIG. 1.

FIG. 4 is a flowchart to explain the measuring function of the device according to embodiments of the invention as shown in FIG. 3.

FIG. 5 is a generalized version of the flowchart of FIG. 4.

FIG. 6 is a simplified representation of the device according to the invention in a further embodiment.

FIG. 7 is a further simplified representation of the device according to embodiments of the invention according to FIG. 1.

FIG. 8 is a simplified representation of the device according to the invention in a further embodiment.

FIG. 9 is a simplified representation of the device according to the invention in a further embodiment.

FIG. 10 is a simplified representation of the device according to the invention in a further embodiment.

FIG. 11 is a simplified representation of the device according to the invention in a further embodiment.

DETAILED DESCRIPTION OF THE DISCLOSED EMBODIMENTS

In the following description, the same reference numbers are used for the same parts and parts with the same action.

Figure 1:
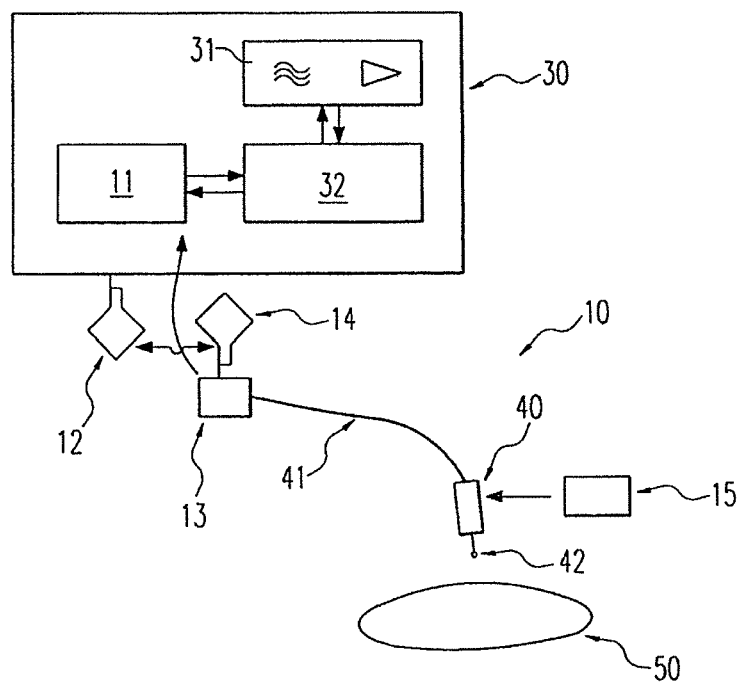
FIG. 1 is an embodiment of the device according to the invention with a surgical apparatus and instrument connected thereto.

FIG. 1 shows a first embodiment of the arrangement according to the invention with an RFID system. This shows a surgical apparatus 30 to which is connected a surgical instrument 40 for treating biological tissue 50. Here, the instrument is intended for monopolar HF surgery and therefore comprises a needle electrode 42 (a corresponding neutral electrode is not shown). The surgical apparatus 30 encompasses an HF generator 31 to provide high-frequency current. Arranged in the surgical apparatus 30, there is a writing and/or reading device 11, which in turn is assigned an antenna for the apparatus 12. The writing and/or reading device. 11 is connected to a control and evaluation device 32 and the control and evaluation device 32 is in turn connected to the HF generator 31. The writing and/or reading device 11 and the control and evaluation device 32 can also be embodied integrally with each other.

The instrument 40 or an instrument connector to connect the instrument to the surgical apparatus 30 is embodied with a writable and readable memory device 13, here for example, with an RFID transponder or tag with an antenna for the instrument 14. The instrument 40 is assigned a measuring and/or actuating device 15, which in turn is assigned, for example, a sensor and/or an actuator on and/or in the instrument (neither shown).

The surgical instrument 40 is supplied via the HF generator 31 with current through the instrument cable 41 so that corresponding treatment may be performed on the patient (for example, coagulation). Here, the measuring and/or actuating device 15 is, for example, assigned a sensor, which, for example, measures the temperature at the electrode 42. This temperature value may be used to obtain information on the progress of the treatment or possible risks (for example, the risk of burning). The connection of the instrument to the HF surgical apparatus via the cable 41 is here only indicated by the arrow pointing into the apparatus.

Since the instruments are operated by means of standard cables with, for example, 3-pin connectors, it is difficult to transmit additional information such as, for example, the measured value (here temperature) over the cable as well. Insofar, the writing and/or reading device 11 with the antenna for the apparatus 12 and the writable and readable memory device 13 with the antenna for the instrument 14 are provided over which the additional information is transmitted by radio, i.e., by means of wireless communication using RFID technology. Locating the transponder in the instrument cable's connector ensures optimum transmission of the information since the antenna for the apparatus and antenna for the instrument are arranged close to each other. However, in principle, the transponder could also be arranged on the instrument.

The at least one measured value transmitted from the instrument 40 to the surgical apparatus 30 can now be evaluated by the control and evaluation device 32 and "forwarded" in such a way that, for example, the voltage at the HF generator 31 is automatically changed—on the basis of the acquired temperature—if this is necessary.

The writing and/or reading device 11 with the antenna for the apparatus 12 and the writable and readable memory device 13 with the antenna for the instrument 14 form the substantial part of the device 10 for contactless communication (RFID system) between the surgical apparatus 30 and the instrument 40. This device is then assigned the measuring and/or actuating device via which additional information or data may be received and also read in order to optionally effect reactions on the surgical apparatus and/or on the instrument.

Figure 2:
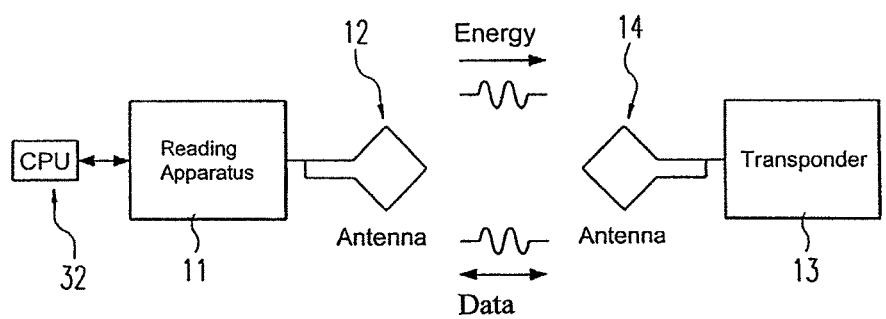
FIG. 2 is a simplified representation of the device according to embodiments of the invention with the writing and/or reading device and writable and readable memory device to explain the basic principle of the device.

FIG. 2 shows a simplified representation of the device according to the invention and explains the basic principle of wireless communication. The transponder 13 with the antenna for the instrument 14 and the writing and/or reading device 11 with the antenna for the apparatus 12 interact in such a way together that, on the one hand, it is possible to transmit data in both directions by radio but, on the other hand, energy is also transmitted at least from the surgical apparatus to the instrument.

FIG. 3 shows a simplified representation of the device 10 according to the invention with the surgical apparatus 30 and instrument 40 to explain the measuring function according to FIG. 1. Here, 'radio system' or 'RFID system' in particular means the writing and/or reading device 11 with the antenna for the apparatus 12 on the one hand and the writable and readable memory device 13 with the antenna for the instrument 14 on the other hand. The sensor 16 receives a sensor signal on and/or in the instrument 40 and/or on the tissue to be treated 50; this is processed accordingly and transmitted via the radio system to the surgical apparatus 30. The control and evaluation device 32, for example a microprocessor, provides the transmitted signal in such a way that settings are made on the surgical apparatus 30 which ensure optimum operation of the instrument 40 as feedback to the at least one acquired measured value. Here, the setting can be made manually (by showing the measurement on a display) or the settings on the surgical apparatus can be made automatically. This relieves the operator of the responsibility for decision-making.

FIG. 4 shows the radio transmission sequence in a flowchart, wherein the radio link is also shown in more detail. The instrument desired by the operator is plugged into the surgical apparatus (step 102). The RFID tag is recognised by the system (step 104), i.e., the contents of the writable and readable memory device are read out by the writing and/or reading device. The radio link can be used to supply the tag and sensor with energy (step 106), so that for example, it is possible to measure the temperature or the pressure (for, example, in water jet surgery) by means of the measuring device (step 108). Finally, the value determined in this way is again transmitted by radio to the surgical apparatus or to the writing and/or reading device (step 110) so that the surgical apparatus (in this case the HF generator) can be suitably regulated or controlled on the basis of the measurement and in this way the instrument, for example, may be supplied with the corresponding parameters (step 112).

In the simplest case; the recognition of the tag represents a read-out from the memory device (in order, for example, to recognise the instrument), but it also can initiate all further necessary processes as long as these are provided (for example, the activation of the measuring device).

FIG. 5 shows a generalized version of the flowchart of FIG. 4. This representation substantially corresponds to that of FIG. 4, but here the measuring device or the sensor is generally replaced by "electronics" (step 114). This makes it clear that not only a measuring device is able to supply additional information to be transmitted by radio link to the surgical apparatus. Instead, this representation is intended to indicate that the transponder component comprises not only the writable and readable memory area, but also additional digital and analog interfaces with which electronic components can be quite generally operated and evaluated on and/or in the instrument. For example, here, it is also possible to provide actuators which receive signals (step 116) from the surgical apparatus and hence take on a function on the instrument.

The arrow pointing upward (in both FIG. 4 and FIG. 5) shows that the regulation or control may be repeated in accordance with a continuous loop.

FIG. 6 shows a simplified representation of the device according to the invention in a further embodiment. The mode of operation of the RFID arrangement was described above. Here, once again, the instrument comprises a measuring and/or actuating device 15. To this is assigned, for example, a sensor 16 arranged in the instrument 40, which is able, for example, to receive the temperature of an electrode or the water pressure of an application probe for water jet surgery. On the basis of the measured value, which can be transmitted by radio to the writing and/or reading device 11 of the surgical apparatus 30, following the appropriate setting, said apparatus can provide the suitable parameters for the further operation of the instrument 40. The control and evaluation device is not shown explicitly here.

On the basis of the transmission of the measured value and of the subsequent setting of the surgical apparatus 30, the suitable parameters for the operation of the instrument 40 are then fed, for example, via the instrument cable to the instrument 40. It is also possible, within a certain framework, to provide the power supply for the electronics on the instrument by radio. Obviously, it is also possible to use tags which are supplied with power by a battery, for example. In addition, it is possible to transmit one command only for the actuation of the instrument 40 by radio from the surgical apparatus 30 to the instrument 40. All combinations of information transmission are conceivable here.

FIG. 7 shows a further simplified representation of the device according to the invention such as is also substantially shown in FIG. 1. The arrangement is similar to that shown in FIG. 6, but here the transponder component 13 is embodied in the instrument cable 41, preferably in a connector to connect the instrument 40 to the surgical apparatus 30. This ensures an optimum radio link because the antennas 12, 14 are arranged close and in a substantially fixed position in relation to each other. Here, the sensor 16 is provided in the instrument in order, for example, to acquire the temperature of an electrode during treatment. In addition, here, a sensor 17 is arranged in the instrument cable in order, for example, to acquire the checking of the plug-in connection. Once again, this can be initiated via the measuring and/or actuating device.

FIG. 8 shows a simplified representation of the device according to the invention in a further embodiment. Instead of sensors, here, for example, switches 20, 21 are shown on the surgical instrument 40. Here, the measuring device or the measuring and/or actuating device 15 can, for example, establish the actuation of one of the switches 20, 21 by the operator so that corresponding information can be transmitted to the writing and/or reading device 11 of the surgical apparatus 30. Subsequently, necessary settings can be made on the surgical apparatus (in connection with the actuated switches)—either automatically by the system or by the operator, for example, because corresponding data are displayed on the surgical apparatus.

It is also possible for the switch 20, 21 to serve as an actuator, which can be actuated via the surgical apparatus by the RFID system. In principle, the actuator could obviously also be controlled via a conventional signal line (because, for example, a parameter transmitted from the instrument to the surgical apparatus via the RFID system requires this).

FIG. 9 shows a simplified representation of the device according to the invention in a further embodiment. The arrangement is similar to that shown in FIG. 8, but here the transponder component 13 is again arranged in the instrument cable 41, for example, in the connector. A first switch 20 is also arranged in the connector, while a second and a third switch 22, 23 are provided on the instrument 40. Here, the actuation of one of the switches by the user, for example, the switch 20 on the connector, can activate the measuring device 15. The actuation of switches 22, 23 on the instrument 40 (for example, to activate said instrument) can, for example, be acquired by the measuring device 15 of the instrument 40 so that a corresponding signal can be transmitted via the RFID system to the surgical apparatus (or the writing and/or reading device).

FIGS. 10 and 11 show further embodiments of the invention. FIG. 10 shows that a coding element 25 (or generally an electronic or electric circuit) is arranged, for example, in the instrument cable 41 together with the writable and readable memory device 13. The coding element 25 provides, for example, information on the type of instrument (instrument recognition) so when the instrument 40 is plugged into the surgical apparatus 30, all necessary parameters for the operation of the instrument on the surgical apparatus are set automatically.

In FIG. 11, a coding element 26 is arranged in the actual instrument 40 and can, for example, be acquired by the measuring device 15 so that the corresponding information can be transmitted to the surgical apparatus 30.

The operation of the arrangement according to FIGS. 10 and 11 is also possible without a measuring and/or actuating device. The arrangement according to FIGS. 8 and 9 is also possible without an explicit measuring device; hence, it is also possible for only the actuating device to be provided.

The RFID system also makes it possible to ensure that operational data is stored during the use of the surgical system. For example, it is possible to check the observance of a maximum permissible number of uses of the instrument or an accessory. It is also possible to receive further information in the memory device, such as, for example, operational data, found to be useful during treatment. These data can then optionally be used as a basis for further action or used for comparison with current measured values and in this way form a sort of reference basis.

The arrangement according to the invention makes it possible to transmit a large amount of information between an instrument and a receiver, in particular a writing and/or reading device with a corresponding antenna in a surgical apparatus, without the need for additional connecting lines. Since, data transmission is possible in both directions, information can be transmitted, on the one hand, from the instrument to the surgical apparatus and, on the other hand, from the surgical apparatus to the instrument by radio. The measuring device or the measuring and/or actuating device can also be supplied at least partially by radio.

The receiver does not necessarily have to be assigned to a surgical apparatus. An autoclave can also comprise a corresponding receiver device. This would make it possible to acquire data from an instrument or enter data into the memory device even if the instrument is not connected to the surgical apparatus, in particular by means of an electrical connection.

The invention claimed is:

1. A device for contactless communication between a surgical apparatus and at least one surgical instrument, the device comprising:
a surgical apparatus that includes a control and evaluation device having at least one reading device which is connected to an antenna for the at least one reading device; and
at least one surgical instrument to which is assigned at least one writable and readable memory device which is connected to an antenna for the at least one writable and readable memory device and is at least partially embodied in a connecting cable arranged to connect the at least one surgical instrument to the surgical apparatus, the at least one surgical instrument comprising:
at least one sensor; and
a measuring device configured to acquire at least one parameter from the at least one sensor,
wherein the at least one writable and readable memory device is designed as a transponder IC with a freely programmable microprocessor and is configured to send the at least one parameter to the reading device of the surgical apparatus via a radio link, and
wherein the control and evaluation device is configured to evaluate the at least one parameter, generate an instruction for controlling an operation of the at least one surgical instrument based on the at least one parameter and to send the instruction to the at least one writable and readable memory device via the radio link.

2. The device according to claim 1, wherein the measuring device is assigned at least one actuator arranged on the instrument for influencing the instrument function.

3. The device according to claim 2, wherein the measuring device is embodied in such a way that the acquisition of the at least one parameter and the influencing the function of the instrument can be performed independently of each other.

4. The device according to claim 2, wherein the measuring device is embodied in such a way that the influencing the function of the instrument takes place on the basis of an acquired parameter.

5. The device according to claim 1, wherein the measuring device is embodied in the instrument or in the connecting cable in order to connect the instrument to the surgical apparatus.

6. The device according to claim 1, wherein the measuring device is embodied in such a way that it acquires the actuation of a switch on the instrument as the at least one parameter.

7. The device according to claim 1, wherein the surgical apparatus and the instrument are embodied for water jet surgery and the measuring device is embodied and arranged in such a way that the pressure in a feed line for supplying water to the tissue to be treated of a water jet applicator can be acquired as a parameter via the sensor.

8. The device according to claim 1, wherein the surgical apparatus and the instrument are embodied for HF surgery and the measuring device is embodied and arranged in such a way that the temperature of an electrode of an HF surgical instrument can be acquired as a parameter during usage via the sensor.

9. The device according to claim 1, wherein the writable and readable memory device is embodied in such a way that data from the instrument relating to sterilisation cycles, storage life, instrument identification or similar data can be read-in and read-out.

10. The device according to claim 1, wherein the instrument comprises at least one coding element which is assigned to the writable and readable memory device and which is embodied in such a way that a coding for the identification of the instrument can be acquired by the reading device on the surgical apparatus.

11. The device according to claim 10, wherein the reading device with the antenna for the apparatus is embodied in such a way that the data from the instrument or the coding can be acquired through a packaging of the instrument.

12. The device according to claim 11, wherein the packaging of the instrument is a sterile packaging.

13. The device according to claim 1, wherein the transponder IC and the sensor are supplied with energy by means of the radio link.

14. A system for contactless communication between a surgical apparatus and at least one surgical instrument, the system comprising:

a high frequency (HF) surgical apparatus that includes a control and evaluation device having at least one reading device which is connected to an antenna for the at least one reading device; and at least one HF surgical instrument having an electrode and at least one writable and readable memory device connected to an antenna for the at least one writable and readable memory device and is embodied in a connecting cable to connect the HF surgical instrument to the HF surgical apparatus, the at least one surgical instrument comprising:

at least one temperature sensor configured to acquire the temperature of the electrode of the HF surgical instrument during operation of the HF surgical instrument; and a measuring device configured to acquire from the at least one temperature sensor at least one parameter, wherein the at least one writable and readable memory device with the antenna for the instrument is designed as a transponder IC with a programmable microprocessor and is configured to send the at least one parameter to the reading device of the surgical apparatus via a radio link, wherein the transponder IC and the at least one temperature sensor are supplied with energy by means of the radio link, and wherein the control and evaluation device is configured to evaluate the at least one parameter, generate an instruction to control the instrument based on the at least one parameter and send the instruction to the at least one writable and readable memory device via the radio link.

15. A system for contactless communication between a surgical apparatus and at least one surgical instrument, the system comprising:

a surgical apparatus that includes a control and evaluation device having at least one reading device which is connected to an antenna for the at least one reading device; and at least one surgical instrument with at least one writable and readable memory device which is connected to an antenna for the at least one writable and readable memory device and is embodied in a connecting cable to connect the at least one surgical instrument to the surgical apparatus, the at least one surgical instrument comprising:

at least one switch for acquiring an input from a user; and a measuring device configured to acquire from the at least one switch at least one parameter, wherein the at least one writable and readable memory device is designed as a transponder IC with a programmable microprocessor and is configured to send the at least one parameter to the reading device of the surgical apparatus via a radio link, wherein the transponder IC and the sensor are supplied with energy by means of the radio link, and wherein the control and evaluation device is configured to evaluate the at least one parameter, generate an instruction to control the surgical apparatus based on the at least one parameter and send the at least one parameter to the at least one writable and readable memory device via the radio link.

16. A system for contactless communication between a surgical apparatus and at least one surgical instrument, the system comprising:

a water jet apparatus that includes a control and evaluation device having at least one reading device which is connected to an antenna for the at least one reading device; and at least one water jet surgical instrument with at least one writable and readable memory device which is connected to an antenna for the at least one writable and readable memory device and is embodied in a connecting cable to connect the instrument to the surgical apparatus, the connecting cable providing pneumatic or liquid connection, wherein the at least one writable and readable memory device is designed as a transponder IC with a programmable microprocessor and is configured to send the at least one parameter to the reading device of the surgical apparatus via a radio link, wherein the instrument comprises at least one pressure sensor for acquiring the pressure in a feed line of the water jet surgical instrument and a measuring device, the measuring device configured to acquire from the at least one sensor at least one parameter, namely the pressure in the feed line, to be transmitted to the surgical apparatus via the radio link, wherein the transponder IC and the sensor are supplied with energy by means of the radio link, and wherein the control and evaluation device is configured to evaluate the at least one parameter, generate an instruction to the control water jet apparatus based on the at least one parameter and send the instruction to the at least one writable and readable memory device via the radio link.

* * * * *